(12) United States Patent
Ozawa

(10) Patent No.: US 8,175,357 B2
(45) Date of Patent: May 8, 2012

(54) X-RAY DIAGNOSTIC APPARATUS, IMAGE PROCESSING APPARATUS, AND IMAGE PROCESSING METHOD

(75) Inventor: Masahiro Ozawa, Sakura (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1015 days.

(21) Appl. No.: 12/038,401

(22) Filed: Feb. 27, 2008

(65) Prior Publication Data
US 2008/0205591 A1 Aug. 28, 2008

(30) Foreign Application Priority Data

Feb. 28, 2007 (JP) ................. 2007-050699

(51) Int. Cl.
*G06K 9/00* (2006.01)
(52) U.S. Cl. ...... 382/130; 382/218; 382/294; 378/98.11
(58) Field of Classification Search .................. 382/130, 382/132, 218, 287, 291, 294, 295; 378/4–20, 378/98.11, 98.12
See application file for complete search history.

(56) References Cited

U.S. PATENT DOCUMENTS
2007/0201609 A1* 8/2007 Ohishi et al. ............... 378/4

FOREIGN PATENT DOCUMENTS
| JP | 03-068348 | 3/1991 |
| JP | 2000-116789 | 4/2000 |
| JP | 2003-143479 | 5/2003 |
| JP | 2004-208306 | 7/2004 |
| JP | 2005-87633 | 4/2005 |
| JP | 2007-229473 | 9/2007 |

OTHER PUBLICATIONS

Japanese Notice of Reasons for Rejection, notice date Nov. 21, 2011 for application No. 2007-050699 (with English translation).

* cited by examiner

*Primary Examiner* — Courtney Thomas
(74) *Attorney, Agent, or Firm* — Oblon, Spivak, McClelland, Maier & Neustadt, L.L.P.

(57) ABSTRACT

A storage unit stores data of a blood vessel image, a first mask image, and a second mask image of an object, an imaging unit which images a fluoroscopic image for the object. A subtraction unit subtracts the first mask image from the fluoroscopic image and generates data of a subtraction image. A calculating unit calculates anatomical displacement amount between the first mask image and the second mask image. A display unit displays the blood vessel image and the subtraction image so as to be superimposed each other by positioning the blood vessel image and the subtraction image to be fitted together on the basis of the calculated displacement amount.

12 Claims, 6 Drawing Sheets

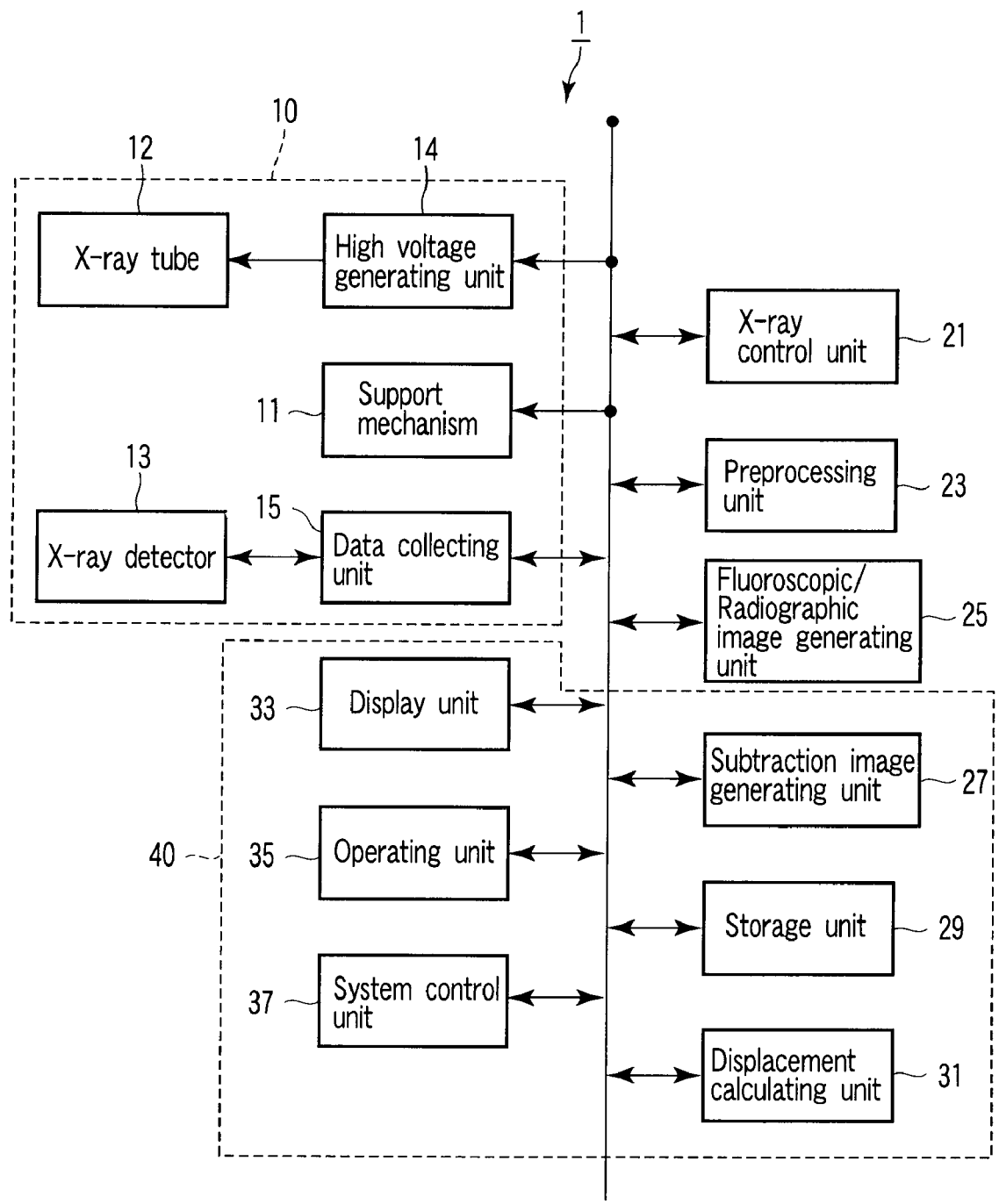
F I G. 1

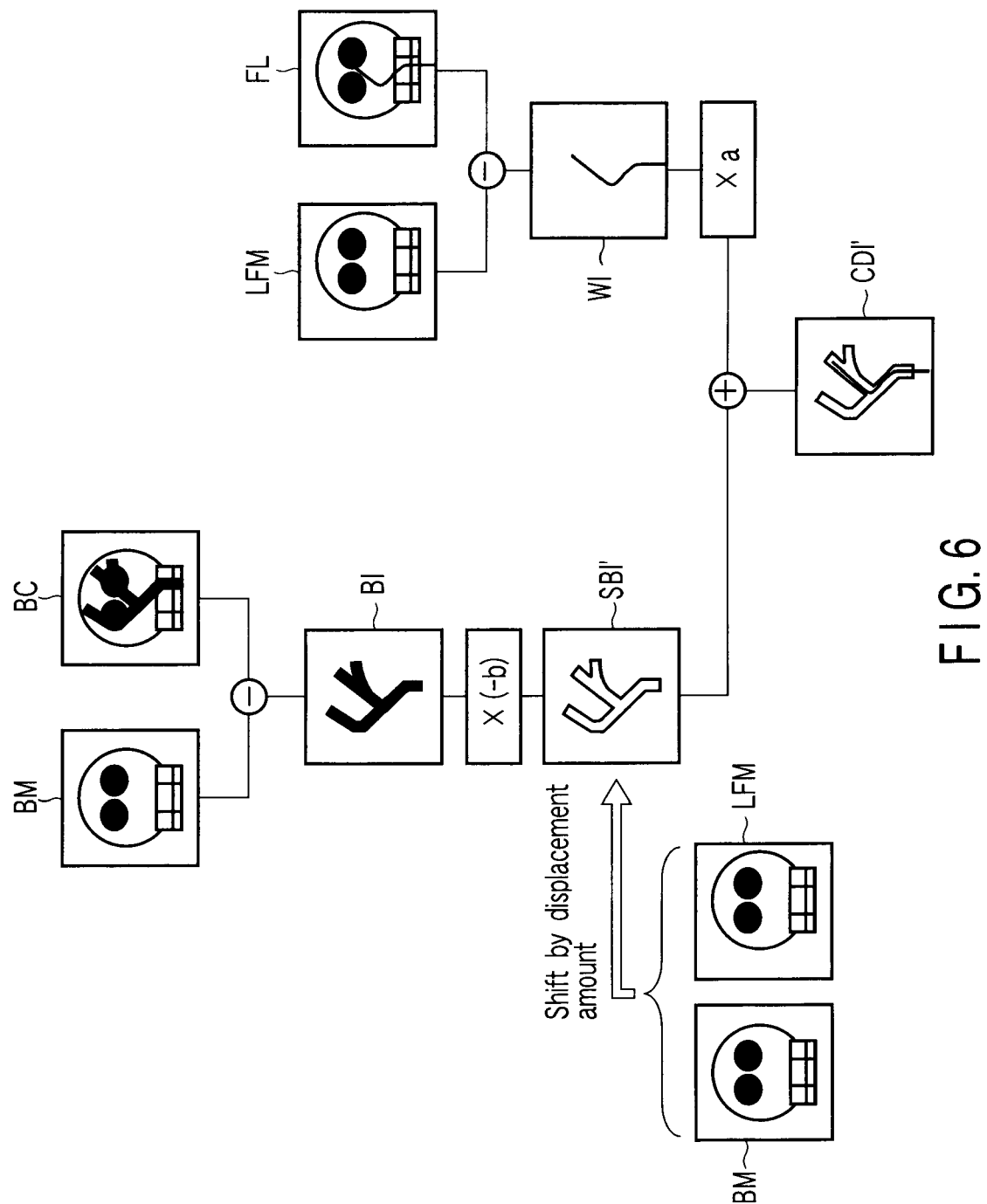
F I G. 6

X-RAY DIAGNOSTIC APPARATUS, IMAGE PROCESSING APPARATUS, AND IMAGE PROCESSING METHOD

CROSS-REFERENCE TO RELATED APPLICATIONS

This application is based upon and claims the benefit of priority from prior Japanese Patent Application No. 2007-050699, filed Feb. 28, 2007, the entire contents of which are incorporated herein by reference.

BACKGROUND OF THE INVENTION

1. Field of the Invention

The present invention relates to an X-ray diagnostic apparatus, an image processing apparatus, and an image processing method, which process an image obtained by X-ray radiography and X-ray fluoroscopy.

2. Description of the Related Art

There are generally two methods of generating an X-ray image by means of an X-ray diagnostic apparatus. One is a method using X-ray radiography and another is a method using X-ray fluoroscopy. Upon X-ray radiography, the X-ray diagnostic apparatus generates an X-ray having a dose enough to obtain a sufficient contrast in a single moment and generates an X-ray image. The X-ray image obtained by the X-ray radiography is referred to as a radiographic image. The radiographic image is an image having a high contrast, a high space resolution, and a high degree of accuracy. On the other hand, upon X-ray fluoroscopy, the X-ray diagnostic apparatus continuously generates less X-rays than the case of the X-ray radiography and continuously generates an X-ray image. The X-ray image obtained by the X-ray fluoroscopy is referred to as a fluoroscopic image. The fluoroscopic image is generated with X-rays less than that in the case of radiographic image is generated, so that it is possible to decrease amount of suffering from X-rays to a patient (object) and an operator. The fluoroscopic image is displayed as a moving image.

On the X-ray fluoroscopy, a treatment may be carried out by inserting a catheter, a guide wire or the like (hereinafter, for simplification, referred to as a wire) into an intended part of a body of a patient. In this case, it is very difficult to operate the wire only by the X-ray fluoroscopy because a contrast of the wire is very weak. Therefore, as an aid for operation of the wire, there is a roadmap method of generating a blood vessel image and displaying this blood vessel image and a wire image in piles (for example, Jpn. Pat. Appln. KOKAI Publication No. 2005-87633).

Hereinafter, a flow of general processing of this roadmap method will be introduced. At first, an operator inserts a wire into a body of a patient upon X-ray fluoroscopy and promotes the wire to the intended part of the body. This fluoroscopic image having the wire drawn is referred to as a fluoroscopic live image. In addition, a fluoroscopic image having no wire drawn to be generated prior to the fluoroscopic live image is referred to as a fluoroscopic mask image. The X-ray diagnostic apparatus stores a fluoroscopic mask image upon X-ray fluoroscopy. The X-ray diagnostic apparatus generates a wire image as a subtraction image by subtracting the fluoroscopic mask image from the fluoroscopic live image to be continuously generated. The X-ray diagnostic apparatus displays the generated wire image and the blood vessel image generated in advance on X-ray imaging in pile in real time. On this displayed image, the wire moving on a blood vessel is displayed in real time. The operator promotes the wire to the intended part while observing this displayed image.

However, a body motion of the patient may be generated during X-ray fluoroscopy. If the body motion is generated, a displacement is generated between the fluoroscopic live image and the fluoroscopic mask image. As a result, an artifact such as a bone is generated on the wire image. In addition, in accordance with the displacement between the fluoroscopic live image and the fluoroscopic mask image, positions of a blood vessel drawn on the blood vessel image and a wire drawn on the wire image are displaced. As a result, it becomes difficult to observe the display image. In addition, it becomes difficult for the operator to promote the wire to the intended part.

In such a case, an artifact such as a bone is improved by removing the wire from the imaging area, X-ray fluoroscoping the patient once again, and regenerating a fluoroscopic mask image. However, according to this method, the displacement between the blood vessel image and the wire image is not improved. In order to improve this displacement, a new blood vessel image should be further generated. Therefore, an extra time (labor) and an extra radiation exposure are generated.

BRIEF SUMMARY OF THE INVENTION

An object of the invention is to provide an X-ray diagnostic apparatus, an image processing apparatus, and an image processing method, which can provide a display image that is easily observed without regenerating a blood vessel image.

An X-ray diagnostic apparatus according to a first aspect of the present invention comprises: a storage unit which stores data of a blood vessel image, a first mask image, and a second mask image of an object; an imaging unit which images a fluoroscopic image for the object; a subtraction unit which subtracts the first mask image from the fluoroscopic image and generates data of a subtraction image; a calculating unit which calculates anatomical displacement amount between the first mask image and the second mask image; and a display unit which displays the blood vessel image and the subtraction image so as to be superimposed each other by positioning the blood vessel image and the subtraction image to be fitted together on the basis of the calculated displacement amount.

An image processing apparatus according to a second aspect of the present invention comprises: a storage unit which stores data of a blood vessel image, a first mask image, a second mask image, and a fluoroscopic image of an object; a subtraction unit which subtracts the first mask image from the fluoroscopic image and generates data of a subtraction image; a calculating unit which calculates anatomical displacement amount between the first mask image and the second mask image; and a display unit which displays the blood vessel image and the subtraction image so as to be superimposed each other by positioning the blood vessel image and the subtraction image to be fitted together on the basis of the calculated displacement amount.

An image processing method according to a third aspect of the present invention comprises: generating data of a subtraction image by subtracting a first mask image from a fluoroscopic image of an object; calculating anatomical displacement amount between the first mask image and a second mask image of the object; and displaying the blood vessel image and the subtraction image so as to be superimposed each other by positioning them to be fitted together on the basis of the calculated displacement amount.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a configuration of an X-ray diagnostic apparatus according to an embodiment of the present invention;

FIG. 6 is a view showing a flow of image processing in a modified embodiment of the correction processing of FIG. 4.

DETAILED DESCRIPTION OF THE INVENTION

Figure 2:
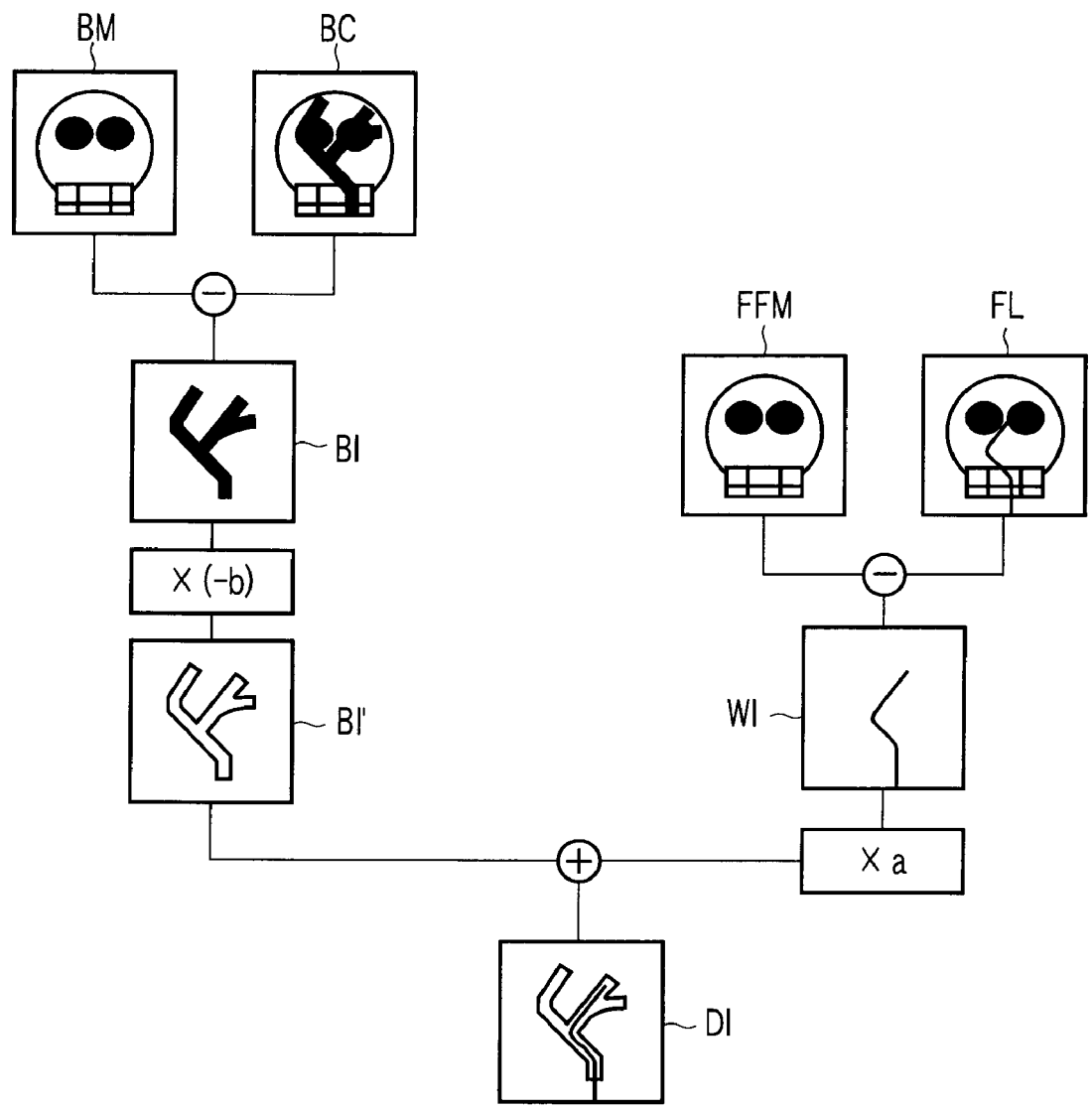
FIG. 2 is a view showing a flow of first processing according to the embodiment.

Hereinafter, an embodiment of the present invention will be described with reference to the drawings.

An X-ray diagnostic apparatus according to the present embodiment can perform X-ray radiography and X-ray fluoroscopy. Upon X-ray radiography, the X-ray diagnostic apparatus generates an X-ray having a dose enough to obtain a sufficient contrast in a single moment and obtains an X-ray image with a good contrast. Upon X-ray fluoroscopy, the X-ray diagnostic apparatus continuously generates X-rays less than that in the case of the X-ray radiography and displays a moving X-ray image.

FIG. 1 is a block diagram of an X ray diagnostic apparatus 1 according to the present embodiment. As shown in FIG. 1, the X ray diagnostic apparatus 1 includes an imaging device 10, an X ray control unit 21, a preprocessing unit 23, a fluoroscopic/radio-graphic image generating unit 25, a subtraction image generating unit 27, a storage unit 29, a displacement calculating unit 31, a display unit 33, an operating unit 35, and a system control unit 37.

The imaging device 10 has a support mechanism 11, an X-ray tube 12, an X-ray detector 13, a high voltage generating unit 14, and a data collecting unit 15. The support mechanism 11 supports the X-ray tube 12 and the X-ray detector 13 so as to be capable of rotating and moving them. The X-ray tube 12 generates an X-ray by being applied with a tube voltage and supplied with a filament current from the high voltage generating unit 14. The X-ray generated from the X-ray tube 12 transmits through a patient mounted on a bed. The X-ray transmitted through the patient is detected by the X-ray detector 13. As the X-ray detector 13, a flat panel detector (FPD) is used. The flat panel detector has a plurality of semiconductor detection devices of a direct conversion type or an indirect conversion type. The semiconductor detection device of the direct conversion type directly converts an incident X-ray into an electric signal. The semiconductor detection device of the indirect conversion type converts the incident X-ray into light by a phosphor and then converts the light into an electric signal. The electric signals converted by a plurality of semiconductor detection devices are collected by the data collecting unit 15 as digital data. As the X-ray detector 13, a combination of an image intensifier and a TV camera may be used.

The X-ray control unit 21 controls the high voltage generating unit 14 so that the X-ray tube 12 may generate X-rays having a dose in accordance with X-ray fluoroscopy and X-ray radiography.

The preprocessing unit 23 preprocesses the digital data transmitted from the data collecting unit 15. The preprocessing includes correction of unevenness in a sensitivity of channels and correction of extreme lowering of a signal intensity or loss of a signal mainly due to an X-ray strong absorber such as a metal portion. The preprocessed digital data is referred to as projection data.

The fluoroscopic/radiographic image generating unit 25 generates X ray image data on the basis of the projection data. An X ray image on the basis of the projection data to be collected upon X ray radiography is referred to as a radiographic image. And an X ray image on the basis of the projection data to be collected upon X ray fluoroscopy is referred to as a fluoroscopic image. The radiographic image and the fluoroscopic image have different contrasts and space resolutions. The contrast and the space resolution of the radiographic image are higher than the contrast and the space resolution of the fluoroscopic image.

The subtraction image generating unit 27 generates subtraction image data by obtaining a difference between two X-ray image data. Specifically, the subtraction image generating unit 27 subtracts the radiographic image data before injecting a contrast agent (the radiographic image data before injecting a contrast agent being hereinafter referred to as blood vessel mask image data) from the radiographic image data in which a blood vessel imaged by the contrast agent is drawn (the radiographic image data in which a blood vessel imaged by the contrast agent is drawn being hereinafter referred to as blood vessel contrast image data) to thereby generate subtraction image data in which the imaged blood vessel is highlighted (subtraction image data in which the imaged blood vessel is highlighted being hereinafter referred to as blood vessel image data). In addition, from fluoroscopic image data having a medical apparatus such as a wire drawn (fluoroscopic image data having a wire drawn being hereinafter referred to as a fluoroscopic live image), the subtraction image generating unit 27 subtracts fluoroscopic image data in which a wire is not drawn (fluoroscopic image data in which a wire is not drawn being hereinafter referred to as fluoroscopic mask image data) to thereby generate subtraction image data in which the wire is highlighted (subtraction image data in which the wire is highlighted being hereinafter referred to as wire image data).

The storage unit 29 stores various X-ray image data to be generated by the fluoroscopic/radiographic image generating unit 25 and the subtraction image generating unit 27. As a configuration of the storage unit 29, a magnetic disk, an optical disk, a magneto-optical disk, a semiconductor memory device or the like may be considered.

The displacement calculating unit 31 calculates an anatomical displacement amount in a body tissue or the like of the patient that is drawn on two X-ray images by using a known technology such as a pixel shift. The anatomical displacement amount is typically a distance that is defined by XY coordinates between the body tissues that are drawn on two X-ray images. Hereinafter, an anatomical position of the body tissue or the like of the patient that is drawn on the X-ray image is simply referred to as a patient position of the X-ray image.

The display unit 33 displays various images to be generated by the fluoroscopic/radiographic image generating unit 25 and the subtraction image generating unit 27. Specifically, the display unit 33 displays a wire image and a blood vessel image to be continuously generated in pile as a moving image. In addition, by shifting the blood vessel image in accordance with the displacement calculated by the displacement calculating unit 31, the display unit 33 displays the shifted blood vessel image and the wire image to be continuously generated in pile.

The operating unit 35 is an input device having a keyboard, various switches, a mouse and the like. For example, the operating unit 35 has a radiography mode button and a fluoroscopy mode button. In addition, the operating unit 35 has a correction button or the like for starting the correction processing to correct the displacement between the blood vessel image and the wire image. The correction processing will be described later.

The system control unit 37 controls various constituent elements in order to realize the operation as the X-ray diagnostic apparatus 1.

In order to support the operation of the wire by the operator, the X-ray diagnostic apparatus 1 having the above-mentioned structure carries out a roadmap method. In the roadmap method, the X-ray diagnostic apparatus 1 generates blood vessel image data and wire image data and displays the blood vessel image and the wire image in pile.

Hereinafter, an example of the processing of the roadmap method by means of the X ray diagnostic apparatus 1 will be described. There are generally two processings according to the present embodiment. The first processing is the same as the processing of the conventional roadmap method. The second processing is carried out after the first processing and is characteristic of the present embodiment. The second processing will be referred to as correction processing. The correction processing is carried out many times according to need. At first, the first processing according to the present embodiment will be described with reference to FIG. 2.

FIG. 2 is a view showing a flow of the first processing according to the present embodiment. On a start point of the processing in FIG. 2, the X-ray diagnostic apparatus 1 is in a radiographic mode. In the radiographic mode, the imaging device 10 generates an X-ray to the object in a single moment. On the basis of the projection data originated in this generated X-ray, the fluoroscopic/radiographic image generating unit 25 generates blood vessel mask image data BM. Next, the operator or the like injects a contrast agent in the patient. Then, in the radiographic mode, the imaging device 10 generates an X-ray to the patient in a single moment. On the basis of the projection data originated in this generated X-ray, the fluoroscopic/radiographic image generating unit 25 generates blood vessel contrast image data BC. Next, the subtraction image generating unit 27 subtracts the blood vessel mask image data BM from the blood vessel contrast image data BC to generate blood vessel image data BI. Then, the blood vessel image data BI is stored in the storage unit 29.

When the subtraction image generating unit 27 terminates generation of the blood vessel image data BI, the operator changes the X-ray diagnostic apparatus 1 into a fluoroscopy mode via the operating unit 35. In the fluoroscopy mode, the imaging devise 10 continuously generates an X-ray. On the basis of the projection data to be collected by continuous generation of the X-ray, the fluoroscopic/radiographic image generating unit 25 continuously generates fluoroscopic image data. In the fluoroscopy mode, the operator injects the wire in the patient and promotes the wire to the intended part in the patient. Further, the fluoroscopic image data before the wire is drawn is stored in the storage unit 29 as first fluoroscopic mask image data FFM. In the X-ray fluoroscopy, the subtraction image generating unit 27 subtracts a fluoroscopic mask image FM from a fluoroscopic live image FL having the wire drawn to generate wire image data WI.

Next, the display unit 33 generates a display image DI by superimposing the wire image WI on the blood vessel image data BI. The display unit 33 then displays the generated display image DI. In this case, the display unit 33 multiplies a coefficient (a) with a pixel value of the wire image data WI and multiplies a coefficient (−b) with a pixel value of the blood vessel image data BI, and then, the display unit 33 superimposes the wire image WI on the blood vessel image BI. The blood vessel image data BI with which the coefficient (−b) is multiplied is referred to as blood vessel image data BI'. The coefficient (a) and the coefficient (−b) are decided in advance. These coefficients are multiplied with the pixel values in order for the blood vessel image BI and the wire image WI to be visible after the superimposition.

The first processing according to the present embodiment is as described above.

In the case where the position of the patient is not displaced in the fluoroscopy mode as shown in FIG. 2, no artifact is generated in the display image DI. However, the position of the patient may be displaced in the fluoroscopy mode. The position of the patient may be displaced, for example, when the patient is shifted (the body motion of the patient is generated) or when the support mechanism 17 is shifted.

Figure 3:
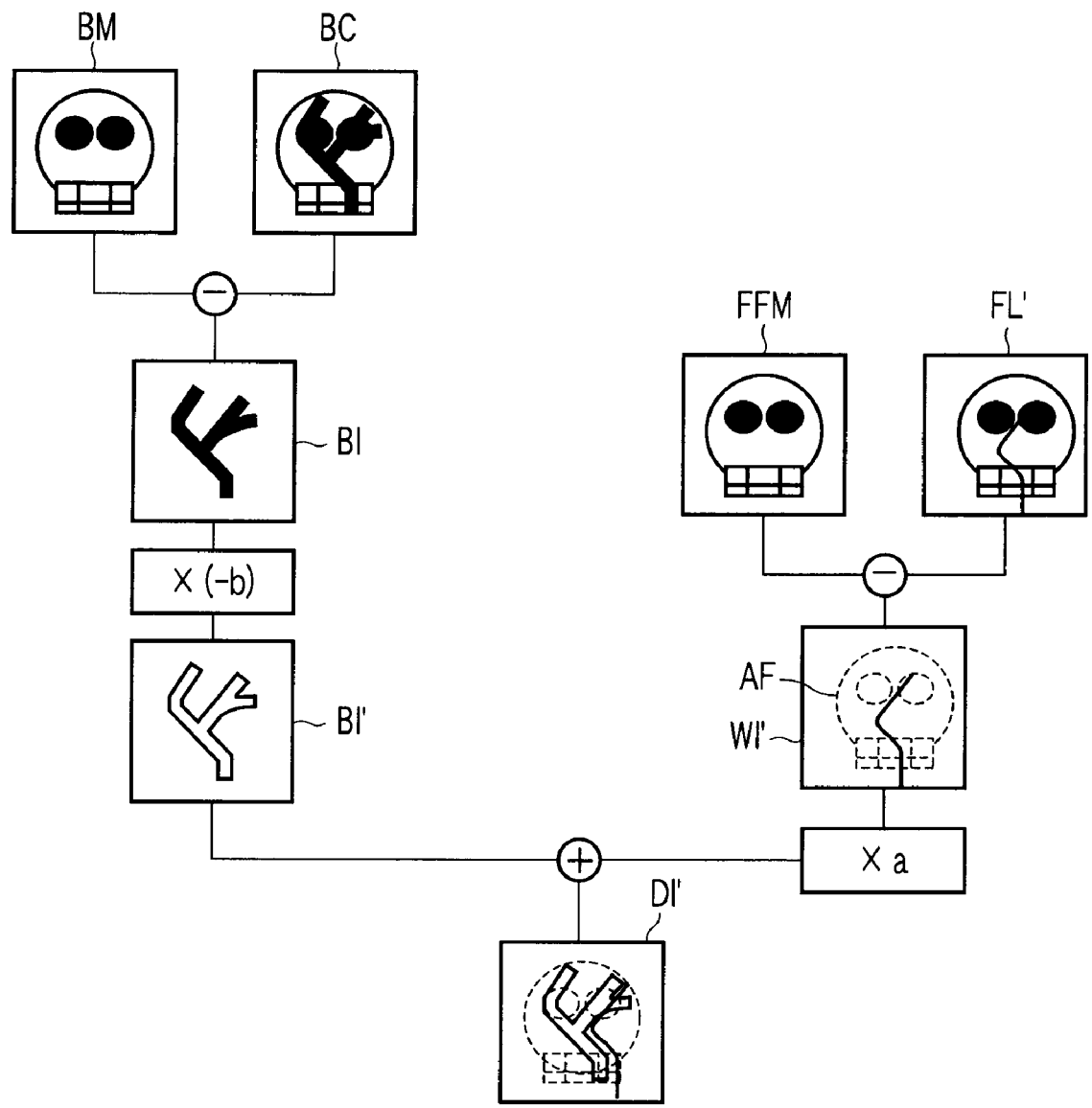
FIG. 3 is a view showing a flow of processing when a body motion of a patient is generated during the processing of FIG. 2.

FIG. 3 is a view showing a flow of the first processing when a body motion of a patient is generated in the fluoroscopy mode. As shown in FIG. 3, when the body motion is generated in the fluoroscopy mode, a displacement is generated between a first fluoroscopic mask image FFM and a fluoroscopic live image FL' after the body motion is generated. As a result, an artifact AF such as a bone is generated in the wire image WI'. In addition, a displacement is generated also between the fluoroscopic live image FL' after the body motion is generated and the blood vessel image BI. Therefore, a display image DI' is obtained by superimposing the wire image WI' and the blood vessel image BI on each other. The generated display image DI' cannot be easily observed.

Figure 4:
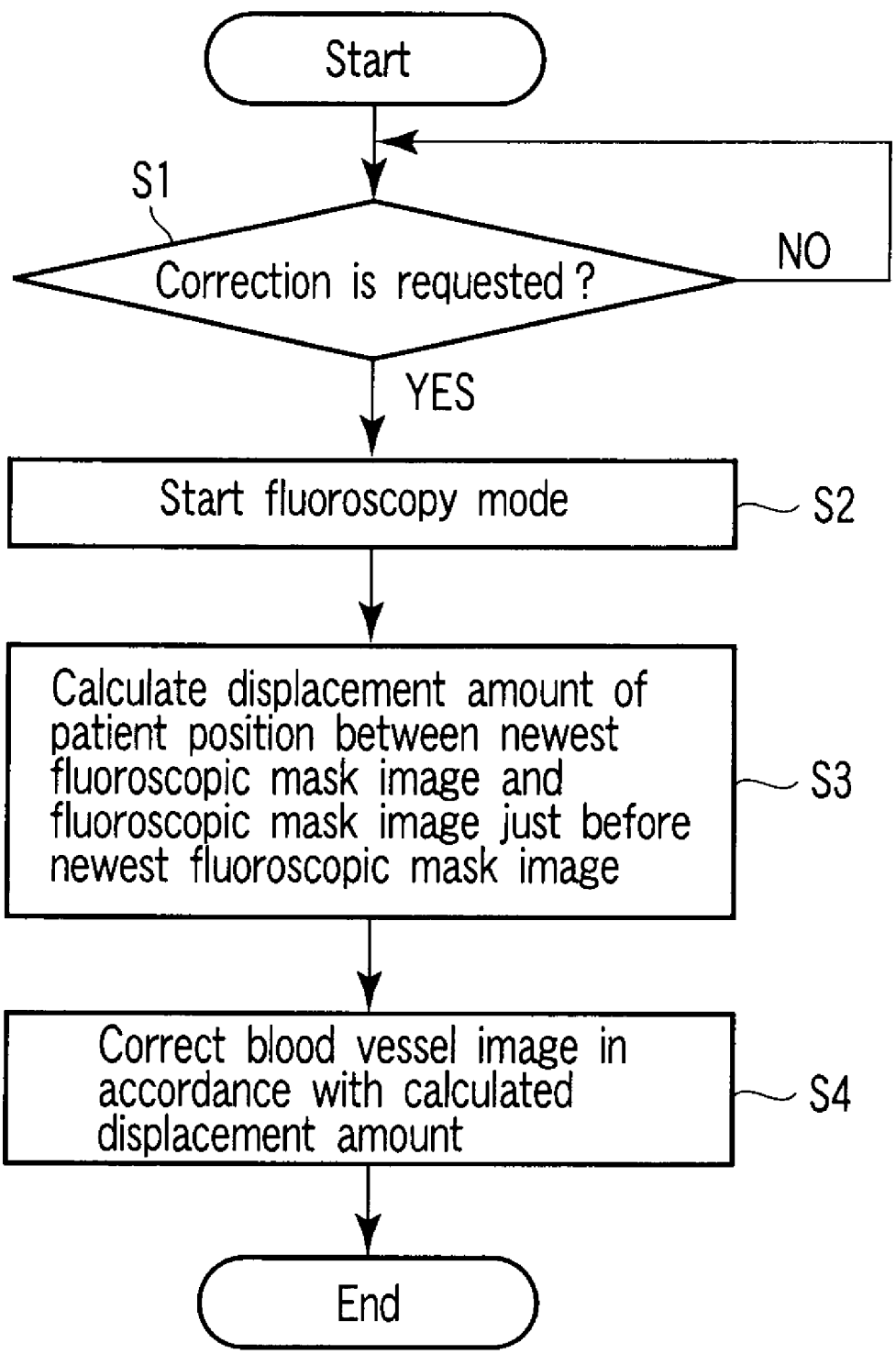
FIG. 4 is a flow chart of the correction processing due to system control unit of FIG. 1.
Figure 5:
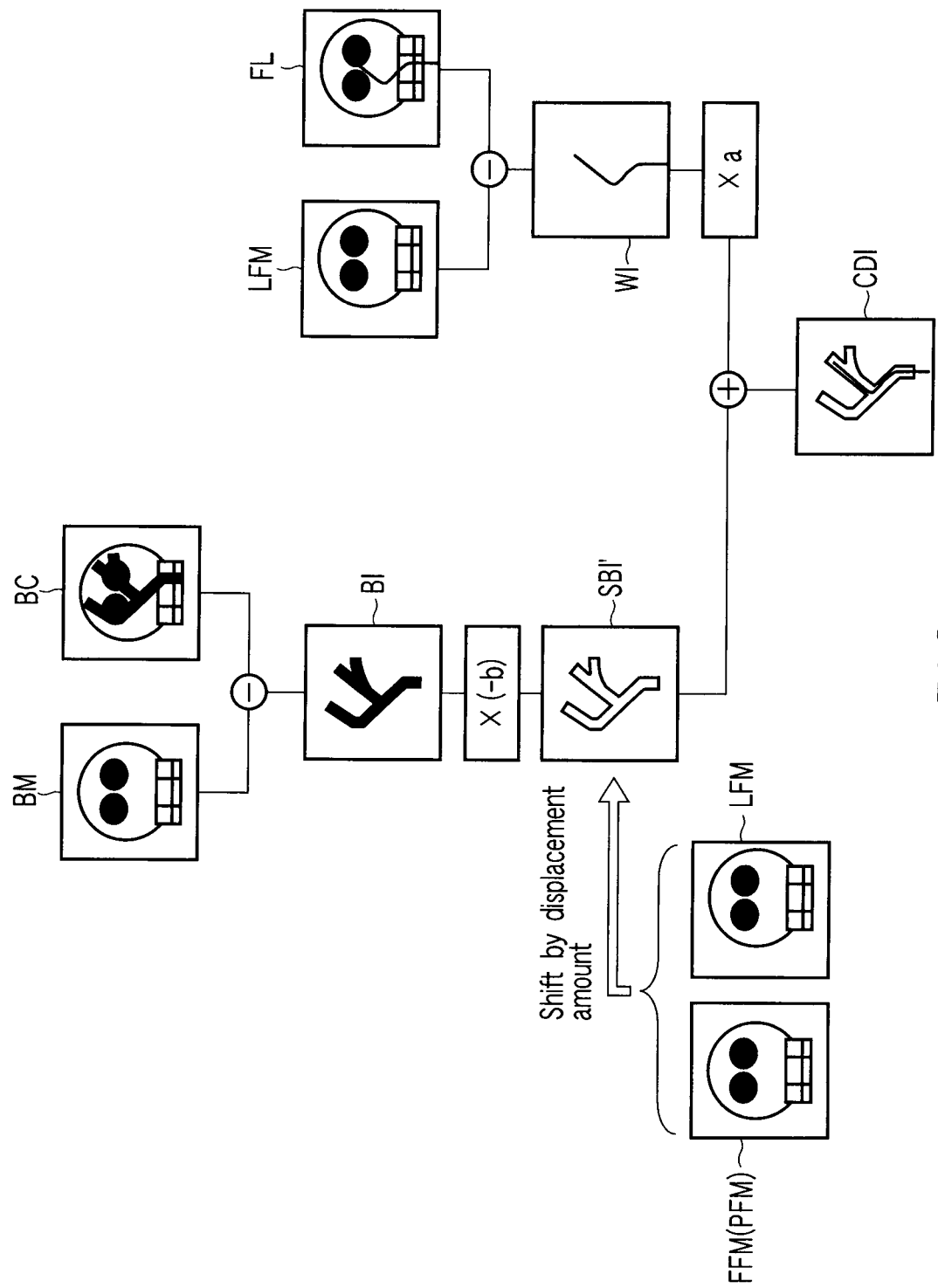
FIG. 5 is a view showing a flow of image processing in the correction processing of FIG. 4.

Hereinafter, correction processing for correcting the artifact and the displacement of the patient position of this display image DI' will be described with reference to FIGS. 4 and 5. FIG. 4 is a flow chart of the correction processing. FIG. 5 is a view showing a flow of the image processing in the correction processing in FIG. 4.

In Step S1, the system control unit 37 stands ready for receiving a correction request from the operator. When the displacement is generated, it is necessary to collect the fluoroscopic mask image data again. The operator then temporarily suspends the fluoroscopy mode by way of the operating unit 35. Subsequently, the operator removes the wire from an imaging area in order to collect the fluoroscopic mask image data again. When these preparations for the correction processing are completed, the operator pushes a correction request button provided in the operating unit 35. When the correction button is pushed, the system control unit 37 is shifted from Step S1 to Step S2.

In Step S2, the system control unit 37 operates the imaging devise 10 so as to start a fluoroscopy mode. In the fluoroscopy mode, the operator promotes the wire toward the intended part of the patient again. In the fluoroscopy mode, the fluoroscopic/radiographic image generating unit 25 continuously generates the fluoroscopic image data. Among a plurality of fluoroscopic mask images to be generated again, the newest fluoroscopic image is referred to as the newest fluoroscopic mask image LFM. In addition, the fluoroscopic image having the wire drawn is referred to as the fluoroscopic live image FL. The newest fluoroscopic mask image data LFM is stored in the storage unit 29.

In Step S3, the system control unit 37 starts displacement calculation processing for the displacement calculating unit 31. In the fluoroscopy mode, the displacement calculating unit 31 calculates the displacement amount in the positions of the patient between the newest fluoroscopic mask image LFM and the first fluoroscopic mask image FFM (or the fluoroscopic mask image generated in the previous correction processing) by using a pixel shift method or the like.

Hereinafter, an example of the pixel shift method will be briefly described. At first, the displacement calculating unit 31 fetches two fluoroscopic mask image data. The displacement calculating unit 31 carries out threshold processing by a desired threshold for the fetched two image data, respectively. As a result of the threshold processing, the two image data are binarized, respectively. One of the binarized two images is defined as a reference image and other is defined as a comparison image. For example, the displacement calculating unit 31 defines the binarized newest fluoroscopic mask image as a reference image. The displacement calculating unit 31 sets a region of interest for the reference image. The displacement calculating unit 31 calculates a product of a pixel value of each pixel included in the region in the reference image and a pixel value of the pixel located on the same position in the comparison image. The displacement calculating unit 31 calculates a summation of products that are calculated for respective images in the region of interest. The calculated summation is defined as an evaluation function. The larger the correlation between the reference image and the comparison image, namely, the more the patient positions of the reference image and the comparison image coincide with each other, the larger the evaluation function. Therefore, the displacement calculating unit 31 calculates an evaluation function by the same method while moving the comparison image little by little. The displacement calculating unit 31 defines the moving amount of the comparison image as the displacement amount when the evaluation function is the highest value.

In Step 4, the system control unit 37 causes the display unit 33 to start the shift processing. In the shift processing, the display unit 33 shifts the blood vessel image data BI', with which the coefficient (−b) is multiplied, by the displacement amount calculated in Step S3. Shifted blood vessel image data SBI' is stored in the storage unit 29. The display unit 33 generates a display image CDI by superimposing this shifted blood vessel image data SBI' and the wire image WI each other. Then, the display unit 33 displays the generated display image CDI. Further, not the blood vessel image data BI but the wire image WI may be shifted.

As shown in FIG. 5, by regenerating the fluoroscopic mask image data in the correction processing, no artifact such as a bone caused by the body motion is generated in the wire image WI. In addition, by shifting the blood vessel image data BI' in accordance with the displacement amount calculated in Step S3, the wire image WI and the shifted blood vessel image data SBI' are positioned so as to be fitted together. In the display image CDI, there is no artifact caused by the body motion and no displacement between the wire image WI and the blood vessel image BI'.

When Step S4 is completed, the system control unit 37 terminates the correction processing. When the system control unit 37 terminates the correction processing, the system control unit 37 starts the correction processing of FIG. 4 again in order to correspond to the next correction processing.

Next, n-th (n≧2) correction processing (hereinafter, referred to as re-correction processing) will be described. There are two kinds of re-correction processing depending on a variation of a target for Subtraction obtained in the displacement calculation. Hereinafter, the first re-correction processing will be described. The same description as the first time is herein omitted.

In n-th Step S2 in the first re-correction processing, the fluoroscopic/radiographic image generating unit 25 generates the newest fluoroscopic mask image data that has been generated in the n-th exposure (hereinafter, referred to as the n-th fluoroscopic mask image data). In n-th Step S3, the displacement calculating unit 31 calculates displacement amount between the n-th fluoroscopic mask image data and the n−1-th fluoroscopic image data. In n-th Step S4, the display unit 33 shifts the blood vessel image that is shifted in n−1-th Step S4 by the displacement amount that is calculated in n-th Step S3. The display unit 33 generates the display image by superimposing this shifted blood vessel image and the wire image each other. Then, the display unit 33 displays the generated display image. As known from Steps S3 and S4, it is necessary for the storage unit 29 to store the blood vessel image that is shifted in Step S4 of the previous re-correction processing.

As described above, in the first re-correction processing, it is defined that the n-th fluoroscopic mask image and the n−1-th fluoroscopic mask image are used in the displacement calculation. However, the second re-correction processing uses the fluoroscopic mask image having substantially the same anatomical positional relation as the blood vessel image in place of the n−1-th fluoroscopic mask image. As such a fluoroscopic mask image, for example, the first fluoroscopic mask image generated in the first processing may be considered. Hereinafter, the second re-correction processing will be briefly described.

In n-th Step S2 of the second re-correction processing, the fluoroscopic/radiographic image generating unit 25 generates the n-th fluoroscopic mask image data. In n-th Step S3, the displacement calculating unit 31 calculates displacement amount between the n-th fluoroscopic mask image and the first fluoroscopic mask image. In Step S4, the display unit 33 shifts the blood vessel image that has been generated at first by the calculated displacement amount. The display unit 33 generates a display image by superimposing this shifted blood vessel image and the wire image. Then, the display unit 33 displays the generated display image. In the second re-correction processing, it is not necessary for the storage unit 29 to store the blood vessel image that is shifted in Step S4. Further, the fluoroscopic mask image to be used for calculation of the displacement is not limited to the first fluoroscopic mask image. As long as it is a mask image obtained in the fluoroscopy mode, any mask image can be used.

In the first re-correction processing, the displacement amount between the n-th fluoroscopic mask image and the n−1-th fluoroscopic mask image is calculated. In the second re-correction processing, the displacement amount between the n-th fluoroscopic mask image and the first fluoroscopic mask image is calculated. It can be regarded that the displacement amount of the patient position between the n-th fluoroscopic mask image and the n−1-th fluoroscopic mask image is smaller than the displacement amount of the patient position between the n-th fluoroscopic mask image and the first fluoroscopic mask image. Therefore, a calculation time of the displacement amount in the first re-correction processing is shorter than that in the second re-correction processing. On the other hand, it is not necessary for the second re-correction processing to store the shifted blood vessel image, so that the data amount of the storage unit 29 may be small.

According to the above-described structure, the displacement calculating unit 31 calculates the displacement amount of the patient position between the first fluoroscopic mask image FFM and the newest fluoroscopic mask image LFM, and then, the display unit 33 displays the blood vessel image SBI' and the wire image WI so as to be superimposed each other by positioning them so as to be fitted together in accordance with the calculated displacement amount. Thus, it is possible for the X ray diagnostic apparatus 1 to provide a display image that can be easily observed without regenerating a new blood vessel image. In addition, as a result, as compared to the case of regenerating a new blood vessel image, the amount of suffering from X rays to the patient and the operator is decreased.

It is not necessary to limit the correction processing to the above-mentioned method, and for example, a modified example as mentioned below may be available. FIG. 6 is a view showing a modified example of the correction processing. As shown in FIG. 6, the displacement amount calculation may be carried out between the newest fluoroscopic mask image data LFM and the blood vessel mask image data BM. In this case, the storage unit 29 stores the generated blood mask image data BM. In Step S3, at first, the displacement calculating unit 31 fits contrasts and space resolutions of the newest fluoroscopic mask image data LFM and the blood vessel mask image data BM together. Then, the displacement calculating unit 31 calculates the displacement amount of the patient position between the newest fluoroscopic mask image data LFM and the blood vessel mask image data BM. In Step S4, the displacement calculating unit 31 shifts the blood vessel image that has been generated at first by the displacement amount calculated in Step S3. The display unit 33 displays a display image CDI' superimposing the shifted blood vessel image SBI' and the wire image WI each other. Then, the display unit 33 displays the generated display image CDI'. It is obvious that the blood vessel mask image BM may be used for the displacement calculation processing in the re-correction processing.

As mentioned in the description of the present embodiment, in the displacement calculation, there are various mask images that are calculated with the newest fluoroscopic mask image. Therefore, the operating unit 35 may be provided with a selection button for selecting a mask image to be calculated with the newest fluoroscopic mask image. A selected mask image is a first-imaged (first-generated) mask image among said plurality of mask images. For example, the operating unit 35 is provided with a first fluoroscopic mask image button, a blood vessel mask image button or the like. When these buttons are pushed, the system control unit 37 causes the displacement calculating unit 31 to start the displacement calculation in accordance with the selected mask image.

In addition, the processing for displaying the blood vessel image and the wire image to be positioned so as to be fitted together according to the present embodiment can be also realized by an image processing apparatus 40 as shown in FIG. 1. As shown in FIG. 1, the image processing apparatus 40 includes the subtraction image generating unit 27, the storage unit 29, the displacement calculating unit 31, the display unit 33, the operating unit 35, and the system control unit 37. For example, the image processing apparatus 40 is comprised of a general-purpose personal computer and a work station. The image processing apparatus 40 is connected to the X-ray diagnostic apparatus 1 via an electric communication line. The storage unit 29 of the image processing apparatus 40 stores various image data generated by the fluoroscopic/radiographic image generating unit 25 of the X-ray diagnostic apparatus 1 via the electric communication line. In addition, the storage unit 29 of the image processing apparatus 40 may obtain the image data from a removable storage medium such as a magnetic disk, an optical disk, a magneto-optical disk, and a semiconductor disk, in which various image data are stored.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X ray diagnostic apparatus comprising:
a storage unit which stores data of a blood vessel image, a first mask image, and a second mask image of an object;
an imaging unit which images a fluoroscopic image for the object;
a subtraction unit which subtracts the first mask image from the fluoroscopic image and generates data of a subtraction image;
a calculating unit which calculates an anatomical displacement amount between the first mask image and the second mask image; and
a display unit which displays the blood vessel image and the subtraction image so as to be superimposed on each other by positioning the blood vessel image and the subtraction image to be fitted together on the basis of the calculated displacement amount.

2. The X ray diagnostic apparatus according to claim 1, wherein the storage unit stores a plurality of mask images including the first mask image and the second mask image, and
the first mask image is the newest mask image among said plurality of mask images.

3. The X ray diagnostic apparatus according to claim 2, wherein the second mask image is a first-imaged mask image among said plurality of mask images.

4. The X ray diagnostic apparatus according to claim 1, wherein the first mask image is an image that is imaged after the second mask image.

5. The X ray diagnostic apparatus according to claim 1, wherein the first mask image has substantially the same anatomical positional relation as the fluoroscopic image.

6. The X ray diagnostic apparatus according to claim 1, wherein the second mask image has substantially the same anatomical positional relation as the blood vessel image.

7. The X ray diagnostic apparatus according to claim 1, wherein, by shifting a blood vessel that is drawn in the blood vessel image by the displacement amount, the display unit generates the shifted blood vessel image and displays the shifted blood vessel image and the subtraction image so as to be superimposed on each other.

8. The X ray diagnostic apparatus according to claim 7, wherein the second mask image is a mask image that is imaged just before the first mask image, and
when the shifted blood vessel image has been generated in the past, the display unit generates a new shifted blood vessel image by further shifting the shifted blood vessel image in accordance with the displacement amount and displays the generated new shifted blood vessel image and the subtraction image so as to be superimposed on each other.

9. The X ray diagnostic apparatus according to claim 1, wherein the blood vessel image is a subtraction image that is generated by subtracting an mask image for the blood vessel image from a contrast image for the blood vessel image, and the second mask image is the mask image for the blood vessel image.

10. The X ray diagnostic apparatus according to claim 3, further comprising a selecting unit which selects a mask image from among the mask images for the blood vessel image or the first-imaged mask image as the second mask image.

11. An image processing apparatus comprising:

a storage unit which stores data of a blood vessel image, a first mask image, a second mask image, and a fluoroscopic image of an object;

a subtraction unit which subtracts the first mask image from the fluoroscopic image and generates data of a subtraction image;

a calculating unit which calculates an anatomical displacement amount between the first mask image and the second mask image; and a display unit which displays the blood vessel image and the subtraction image so as to be superimposed on each other by positioning the blood vessel image and the subtraction image to be fitted together on the basis of the calculated displacement amount.

12. An image processing method comprising:

generating data of a subtraction image by subtracting a first mask image from a fluoroscopic image of an object;

calculating an anatomical displacement amount between the first mask image and a second mask image of the object; and displaying the blood vessel image and the subtraction image so as to be superimposed on each other by positioning them to be fitted together on the basis of the calculated displacement amount.

* * * * *